US009993394B2

(12) United States Patent
Kita et al.

(10) Patent No.: US 9,993,394 B2
(45) Date of Patent: Jun. 12, 2018

(54) DENTAL RESTORATIVE COMPOSITION

(71) Applicant: KURARAY NORITAKE DENTAL INC., Kurashiki-shi (JP)

(72) Inventors: Hirotaka Kita, Tainai (JP); Michiya Kawana, Tainai (JP); Eiichi Terakawa, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 155 days.

(21) Appl. No.: 15/119,053

(22) PCT Filed: Feb. 17, 2015

(86) PCT No.: PCT/JP2015/000733
§ 371 (c)(1),
(2) Date: Aug. 15, 2016

(87) PCT Pub. No.: WO2015/125470
PCT Pub. Date: Aug. 27, 2015

(65) Prior Publication Data
US 2017/0049665 A1 Feb. 23, 2017

(30) Foreign Application Priority Data

Feb. 20, 2014 (JP) ................................. 2014-031029

(51) Int. Cl.
| | | |
|---|---|---|
| A61K 6/08 | (2006.01) |
| A61K 6/02 | (2006.01) |
| A61K 6/083 | (2006.01) |
| A61K 6/027 | (2006.01) |
| A61K 6/00 | (2006.01) |

(52) U.S. Cl.
CPC ............ *A61K 6/083* (2013.01); *A61K 6/0005* (2013.01); *A61K 6/0008* (2013.01); *A61K 6/0052* (2013.01); *A61K 6/027* (2013.01)

(58) Field of Classification Search
CPC ...... A61K 6/0005; A61K 6/027; A61K 6/083; A61K 6/0008; A61K 6/0052; C08L 133/10
USPC ................................................. 523/116, 117
See application file for complete search history.

(56) References Cited

U.S. PATENT DOCUMENTS

| | | | |
|---|---|---|---|
| 4,115,487 A * | 9/1978 | Rockett .................. | A61C 13/09 264/16 |
| 4,388,069 A * | 6/1983 | Orlowski ................ | A61K 6/083 106/35 |
| 4,393,185 A * | 7/1983 | Berner .................... | C08G 59/68 525/507 |
| 5,356,951 A * | 10/1994 | Yearn ..................... | A61K 6/083 523/115 |
| 5,773,489 A * | 6/1998 | Sato ....................... | A61K 6/093 106/35 |
| 6,221,931 B1 * | 4/2001 | Sakuma ................. | A61K 6/0276 428/404 |
| 6,232,367 B1 * | 5/2001 | Kobashigawa ....... | A61K 6/0088 260/998.11 |
| 6,593,395 B2 * | 7/2003 | Angeletakis .......... | A61K 6/0073 433/202.1 |
| 6,933,327 B2 | 8/2005 | Yamakawa et al. | |
| 7,091,258 B2 * | 8/2006 | Neubert ................. | A61K 6/0091 433/212.1 |
| 8,476,338 B2 * | 7/2013 | Okubayashi .......... | A61K 6/0005 106/35 |
| 8,822,564 B2 * | 9/2014 | Drechsler .............. | A61K 6/0008 523/115 |
| 9,320,684 B2 * | 4/2016 | Isizaka .................. | A61K 6/0005 |
| 2003/0036582 A1 * | 2/2003 | Yamakawa ........... | A61K 6/0073 523/115 |
| 2004/0138330 A1 * | 7/2004 | Grundler ............... | A61K 6/0094 523/115 |
| 2011/0077320 A1 * | 3/2011 | Machida ............... | A61K 6/0073 522/182 |
| 2013/0096226 A1 * | 4/2013 | Toriyabe ............... | A61K 6/0091 523/115 |

FOREIGN PATENT DOCUMENTS

| | | |
|---|---|---|
| JP | 9-255516 A | 9/1997 |
| JP | 2002-138008 A | 5/2002 |
| JP | 2007-302631 A | 11/2007 |
| JP | 2012-153640 A | 8/2012 |
| WO | WO 2012/176877 A1 | 12/2012 |

OTHER PUBLICATIONS

International Search Report dated Mar. 31, 2015, in PCT/JP2015/000733 filed Feb. 17, 2015.

* cited by examiner

*Primary Examiner* — Sanza Mcclendon
(74) *Attorney, Agent, or Firm* — Oblon, McClelland, Maier & Neustadt, L.L.P.

(57) ABSTRACT

Provided is a dental restorative composition that has good handling properties when in the form of a paste having yet to be cured and that has light diffusion ability and transparency when in the form of a cured product. The dental restorative composition includes a polymerizable monomer, a polymerization initiator, an inorganic filler (C) having an average particle diameter of 0.1 to 1 μm, an organic-inorganic composite filler (D) having an average particle diameter of 1 μm or more and less than 10 μm, and an organic-inorganic composite filler (E) having an average particle diameter of 10 to 50 μm. An absolute value of a difference between a refractive index (Cd) of the inorganic filler (C) and a refractive index (Ad) of a polymer of the polymerizable monomer is 0.01 or less, an absolute value of a difference between the refractive index (Ad) and one of a refractive index (Dd) of the organic-inorganic composite filler (D) and a refractive index (Ed) of the organic-inorganic composite filler (E) is 0.01 or less, and an absolute value of a difference between the refractive index (Ad) and the other of the refractive index (Dd) and the refractive index (Ed) is 0.03 or more.

4 Claims, No Drawings

DENTAL RESTORATIVE COMPOSITION

TECHNICAL FIELD

The present invention relates to dental restorative compositions and particularly relates to a novel dental restorative composition usable, for example, in resinous prosthetic materials and resinous restorative materials.

BACKGROUND ART

Dental restorative compositions containing a polymerizable monomer, a polymerization initiator, and a filler are called composite resins, and are often used as materials for restoring a missing part of a tooth or treating dental caries in recent dentistry.

The physical properties of such dental restorative compositions depend on factors such as the material, shape, and particle diameter of the filler. An inorganic filler is typically used as the filler; however, the use of organic-inorganic composite fillers has also been studied.

For example, Patent Literature 1 discloses a dental polymerization-curable composition that contains an organic-inorganic composite filler and that can be formed into a dental composite restorative material having good color compatibility with natural teeth. This composition contains an organic-inorganic composite filler having an average particle diameter of 1 to 20 μm and having a refractive index that differs by 0.01 or more from the refractive index of a matrix portion in which the filler is dispersed. A cured product of the composition has high light diffusion ability and therefore excellent color compatibility with natural teeth.

CITATION LIST

Patent Literature

Patent Literature 1: JP 2002-138008 A

SUMMARY OF INVENTION

Technical Problem

However, a study by the present inventors has revealed that when the dental restorative composition disclosed in Patent Literature 1 contains a large amount of the organic-inorganic composite filler, the composition in the form of a paste having yet to be cured may be excessively dry and have poor handling properties or the composition may fail to have sufficient transparency. It has also been found that when the content of the organic-inorganic composite filler is small, the dental restorative composition that has been cured may fail to have sufficient light diffusion ability.

That is, it has not been easy to obtain a dental restorative composition that meets all of the demands for good handling properties of a paste and good light diffusion ability and transparency of a cured product.

It is therefore an object of the present invention to provide a dental restorative composition that has good handling properties when in the form of a paste having yet to be cured and that has good light diffusion ability and transparency when in the form of a cured product.

Solution to Problem

As a result of a detailed study, the present inventors have found that the above object can be achieved, provided that an inorganic filler and two organic-inorganic composite fillers having different predetermined average particle diameters are added to a dental restorative composition and that differences between the refractive index of a polymer of a polymerizable monomer and the refractive indices of the inorganic filler and the organic-inorganic composite fillers are within predetermined ranges.

That is, the present invention provides a dental restorative composition including:
a polymerizable monomer (A);
a polymerization initiator (B):
an inorganic filler (C) having an average particle diameter of 0.1 to 1 μm; and
an organic-inorganic composite filler, wherein
the organic-inorganic composite filler includes
an organic-inorganic composite filler (D) having an average particle diameter of 1 μm or more and less than 10 μm, and
an organic-inorganic composite filler (E) having an average particle diameter of 10 to 50 μm,
an absolute value of a difference between a refractive index (Cd) of the inorganic filler (C) and a refractive index (Ad) of a polymer of the polymerizable monomer (A) is 0.01 or less,
an absolute value of a difference between the refractive index (Ad) and one of a refractive index (Dd) of the organic-inorganic composite filler (D) and a refractive index (Ed) of the organic-inorganic composite filler (E) is 0.01 or less, and
an absolute value of a difference between the refractive index (Ad) and the other of the refractive index (Dd) and the refractive index (Ed) is 0.03 or more.

Advantageous Effects of Invention

The dental restorative composition of the present invention, when in the form of a paste having yet to be cured, has good handling properties and, when in the form of a cured product, has good light diffusion ability and transparency.

DESCRIPTION OF EMBODIMENTS

A dental restorative composition of the present invention includes a polymerizable monomer (A), a polymerization initiator (B), an inorganic filler (C) having an average particle diameter of 0.1 to 1 μm, and an organic-inorganic composite filler, and the organic-inorganic composite filler includes an organic-inorganic composite filler (D) having an average particle diameter of 1 μm or more and less than 10 μm and an organic-inorganic composite filler (E) having an average particle diameter of 10 to 50 μm. The absolute value of the difference between a refractive index (Ad) of a polymer of the polymerizable monomer (A) and one of a refractive index (Dd) of the organic-inorganic composite filler (D) and a refractive index (Ed) of the organic-inorganic composite filler (E) (Dd or Ed) is 0.01 or less, and the absolute value of the difference between the refractive index (Ad) and the other of the refractive indices (Ed or Dd) is 0.03 or more.

Hereinafter, the ingredients used in the present invention will each be described. In the present description, "methacryl" and "acryl" are collectively referred to as "(meth)acryl". The term "(meth)acrylate" refers to an acrylic acid ester and/or a methacrylic acid ester.

The polymerizable monomer (A) is not particularly limited, and a commonly-known material can be used as the polymerizable monomer (A). For example, a radical-polymerizable monomer can be suitably used. Specific examples of the radical-polymerizable monomer include: esters of α-cyanoacrylic acid, (meth)acrylic acid, α-halogenated acrylic acid, crotonic acid, cinnamic acid, sorbic acid, maleic acid, and itaconic acid; (meth)acrylamide; (meth) acrylamide derivatives; vinyl esters; vinyl ethers; mono-N-vinyl derivatives; and styrene derivatives. Among these, (meth)acrylic acid esters are preferred. Examples of the (meth)acrylic acid esters include: a (meth)acrylic acid ester (a-1) having an aromatic ring and having no hydroxyl group; a (meth)acrylic acid ester (a-2) having an aromatic ring and a hydroxyl group; and a (meth)acrylic acid ester (a-3) having neither aromatic ring nor hydroxyl group.

The (meth)acrylic acid ester (a-1) having an aromatic ring and having no hydroxyl group is not particularly limited as long as it is a (meth)acrylic acid ester having an aromatic ring and having no hydroxyl group, and the number of aromatic rings may be at least one. Examples of such a compound include those represented by the following formula (I), where m and n each represent the average number of moles of added ethoxy groups and are zero or a positive number, the sum of m and n is preferably 1 to 6, more preferably 2 to 4, and $R_1$ is hydrogen or a methyl group.

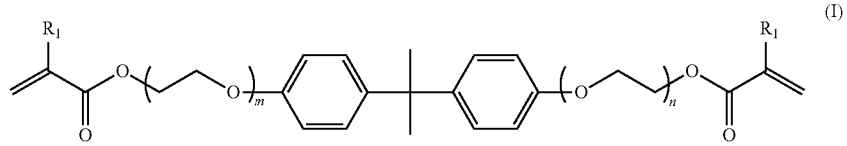

Specific examples include 2,2-bis[4-(meth)acryloyloxy-polyethoxyphenyl]propane in which m+n=2.6 (and which may hereinafter be referred to as "D2.6E"), 2,2-bis[4-(meth)acryloyloxypolyethoxyphenyl]propane in which m+n=6 (and which may hereinafter be referred to as "D6E"), 2,2-bis[4-(meth)acryloyloxydiethoxyphenyl]propane (m+n=2), 2,2-bis[4-(meth)acryloyloxytetraethoxyphenyl] propane (m+n=4), and 2,2-bis[4-(meth)acryloyloxypentaethoxyphenyl]propane (m+n=5). Additional examples include 2,2-bis[(meth)acryloyloxyphenyl]propane, 2,2-bis[4-(meth)acryloyloxydipropoxyphenyl]propane, 2-[4-(meth)acryloyloxydiethoxyphenyl]-2-[4-(meth)acryloyloxyditriethoxyphenyl]propane, 2-[4-(meth)acryloyloxydipropoxyphenyl]-2-[4-(meth)acryloyloxytriethoxyphenyl]propane, 2,2-bis[4-(meth)acryloyloxypropoxyphenyl]propane, 2,2-bis[4-(meth)acryloyloxyIsopropoxyphenyl]propane, and 2,2-bis[4-[3-(meth)acryloyloxy-2-(meth)acryloyloxypropoxy]phenyl] propane.

The (meth)acrylic acid ester (a-2) having an aromatic ring and a hydroxyl group is not particularly limited, as long as it is a (meth)acrylic acid ester having an aromatic ring and a hydroxyl group. The number of aromatic rings and the number of hydroxyl groups are independent of each other, and the number of each functional group may be at least one. Examples of such a compound include 2,2-bis[4[3-(meth)acryloyloxy-2-hydroxypropoxy]phenyl]propane (which may hereinafter be referred to as "Bis-GMA"), 2-[4-[3-(meth)acryloyloxy-2-hydroxypropoxy]phenyl]-2-[4-[2,3-di(meth)acryloyloxypropoxy]phenyl]propane (which may hereinafter be referred to as "Bis3"), 2-[4-[3-(meth)acryloyloxy-2-hydroxypropoxy]phenyl]-2-[4-(meth)acryloyloxydiethoxyphenyl]propane, 2-[4-[3-(meth)acryloyloxy-2-hydroxypropoxy]phenyl]-2-[4-(meth)acryloyloxyditriethoxyphenyl]propane, and 2-[4-[3-(meth)acryloyloxy-2-hydroxypropoxy]phenyl]-2-[4-(meth)acryloyloxydipropoxyphenyl]propane.

Examples of the (meth)acrylic acid ester (a-3) having neither aromatic ring nor hydroxyl group include ethylene glycol di(meth)acrylate, triethylene glycol di(meth)acrylate (which may hereinafter be referred to as "3G"), propylene glycol di(meth)acrylate, neopentyl glycol di(meth)acrylate, 1,6-hexanediol di(meth)acrylate, 1,10-decanediol di(meth) acrylate (which may hereinafter be referred to as "DD"), methyl (meth)acrylate, iso-butyl (meth)acrylate, benzyl (meth)acrylate, lauryl (meth)acrylate, 2-(N,N-dimethylamino)ethyl (meth)acrylate, 2,3-dibromopropyl (meth)acrylate, N,N'-(2,2,4-trimethylhexamethylene)bis[2-(aminocarboxy)ethane-1-ol] dimethacrylate (which may hereinafter be referred to as "UDMA"), N,N'-(2,2,4-trimethylhexamethylene)bis[2-(aminocarboxy)propane-1,3-diol] tetramethacrylate (which may hereinafter be referred to as "U4TH"), (meth)acryloyloxydodecylpyridinium bromide, (meth)acryloyloxydodecylpyridinium chloride, trimethylolpropane (meth)acrylate, trimethylolethane tri(meth)acrylate, and pentaerythritol tetra(meth)acrylate.

The polymerizable monomer (A) is preferably such that the refractive index (Ad) of its polymer is 1.48 to 1.60. The refractive index (Ad) of a polymer of the polymerizable monomer (A) is more preferably in the range of 1.50 to 1.59 and even more preferably in the range of 1.52 to 1.58, in order to adjust the difference of the refractive index (Ad) from the refractive index (Cd) of the inorganic filler (C) to 0.01 or less. A possible way to achieve the desired refractive index after polymerization and curing is to select one appropriate polymerizable monomer as the polymerizable monomer (A) or mix two or more polymerizable monomers having different refractive indices in proper proportions to prepare the polymerizable monomer (A) while taking into account the fact that a polymer of a polymerizable monomer typically has a slightly higher refractive index than the polymerizable monomer. The refractive index (Ad) of a polymer of the polymerizable monomer (A) can be measured by the method described in "EXAMPLES".

One, or a combination of two or more, of the above examples of the polymerizable monomer (A) may be used. Polymerizable monomers known in the field of dental materials can be used as the polymerizable monomer (A) without any limitation. Among the examples of the polymerizable monomer (A), Bis-GMA, D2.6E, 3G, DD, and UDMA are suitable for use in terms of, for example, the refractive index, the mechanical strength of a cured product of the composition, and the handling properties of a paste of the composition.

The polymerization initiator (B) can be selected for use from among generally usable polymerization initiators, among which polymerization initiators for dental use are preferably used. In particular, one polymerization initiator for photopolymerization or chemical polymerization can be used alone, or two or more such polymerization initiators can be used in appropriate combination.

Examples of the photopolymerization initiators include (bis)acylphosphine oxides, thioxanthones, quaternary ammonium salts of thioxanthones, ketals, α-diketones, benzoin alkyl ethers, and α-aminoketones.

The (bis)acylphosphine oxides include acylphosphine oxides and bisacylphosphine oxides. Examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Salts of (bis)acylphosphine oxides such as sodium salts and lithium salts of the above compounds can also be used as the photopolymerization initiator.

Among the above (bis)acylphosphine oxides, 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoyidiphenylphosphine oxide sodium salt are preferable.

Examples of the thioxanthones and the quaternary ammonium salts of thioxanthones include thioxanthone, 2-chlorothioxanthen-9-one, 2-hydroxy-3-(9-oxo-9H-thioxanthen-4-yloxy)-N,N,N-trimethyl-propanaminium chloride, 2-hydroxy-3-(1-methyl-9-oxo-9H-thioxanthen-4-yloxy)-N,N,N-trimethyl-propanaminium chloride, 2-hydroxy-3-(9-oxo-9H-thioxanthen-2-yloxy)-N,N,N-trimethyl-propanaminium chloride, 2-hydroxy-3-(3,4-dimethyl-9-oxo-9H-thioxanthen-2-yloxy)-N,N,N-trimethyl-1-propanaminium chloride, 2-hydroxy-3-(3,4-dimethyl-9H-thioxanthen-2-yloxy)-N,N,N-trimethyl-1-propanaminium chloride, and 2-hydroxy-3-(1,3,4-trimethyl-9-oxo-9H-thioxanthen-2-yloxy)-N,N,N-trimethyl-1-propanaminium chloride.

A preferred thioxanthone among the above thioxanthones is 2-chlorothioxanthen-9-one, and a preferred quaternary ammonium salt of a thioxanthone among the above quaternary ammonium salts of thioxanthones is 2-hydroxy-3-(3,4-dimethyl-9H-thioxanthen-2-yloxy)-N,N,N-trimethyl-1-propanaminium chloride.

Examples of the ketals include benzyl dimethyl ketal and benzyl diethyl ketal.

Examples of the α-diketones include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is preferable in that it shows maximum absorption at a wavelength in the visible region.

Examples of the benzoin alkyl ethers include benzoin methyl ether, benzoin ethyl ether, benzoin isopropyl ether, and benzoin isobutyl ether.

Examples of the α-aminoketones include 2-methyl-1-[4-(methylthio)phenyl]-2-morpholinopropan-1-one.

Among the above photopolymerization initiators, at least one selected from the group consisting of the (bis)acylphosphine oxides, the salts thereof, and the α-diketones is preferably used.

An azo compound or an organic peroxide is preferably used as the chemical polymerization initiator. The azo compound and the organic peroxide are not particularly limited, and commonly-known azo compounds or organic peroxides can be used. A typical example of the azo compound is azobisisobutyronitrile. Typical examples of the organic peroxide include ketone peroxides, hydroperoxides, diacyl peroxides, dialkyl peroxides, peroxyketals, peroxyesters, and peroxydicarbonates.

Examples of the ketone peroxides include methyl ethyl ketone peroxide, methyl isobutyl ketone peroxide, methyl cyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, and t-butyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butyl cumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis-butylperoxy)octane, and n-butyl 4,4-bis(t-butylperoxy)valerate.

Examples of the peroxyesters include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxymaleric acid.

Examples of the peroxydicarbonates include di-3-methoxy peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, the diacyl peroxides are preferably used in view of the overall balance of safety, storage stability, and radical formation potential. Among the diacyl peroxides, benzoyl peroxide is more preferably used.

The polymerization initiator (B) is contained preferably in an amount of 0.01 to 10 parts by weight, more preferably in an amount of 0.1 to 7 parts by weight, even more preferably in an amount of 0.15 to 6 parts by weight, particularly preferably in an amount of 0.5 to 5 parts by weight, per 100 parts by weight of the polymerizable monomer (A).

The dental restorative composition of the present invention may further contain a polymerization accelerator. Examples of the polymerization accelerator include amines, sulfinic acids, sulfinates, aldehydes, and thiol compounds.

The amines are classified into aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N,N-dimethylaminoethyl methacrylate, N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, trimethylamine, triethylamine, and tributylamine. Among these, the tertiary aliphatic amines are preferable in terms of the curability and storage stability of the composition and, in particular, N,N-dimethylaminoethyl methacrylate, N-methyldiethanolamine, and triethanolamine are more preferably used.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-N,N-dimethylaminobenzoate, methyl 4-N,N-dimethylaminobenzoate, n-butoxyethyl N,N-dimethylaminobenzoate, 2-(methacryloyloxy)ethyl 4-N,N-dimethylaminobenzoate, 4-N,N-dimethylaminobenzophenone, and butyl 4-dimethylaminobenzoate. Among these, at least one selected from the group consisting of N,N-di.(2-hydroxyethyl)-p-toluidine, ethyl 4-N,N-dimethylaminobenzoate, n-butoxyethyl N,N-dimethylaminobenzoate, and 4-N,N-dimethylaminobenzophenone is preferably used in terms of the ability to improve the curability of the dental restorative composition.

Examples of the sulfinic acids and sulfinates include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium. 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesuifinic acid, sodium 2,4,6-trimethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesuifinate, and calcium 2,4,6-triisopropylbenzenesulfinate. Among these, sodium benzenesulfinate, sodium p-toluenesulfinate, and sodium 2,4,6-triisopropylbenzenesulfinate are preferably used.

Examples of the aldehydes include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde. Among these, p-n-octyloxybenzaldehyde is preferably used, in terms of the ability to improve the curability of the dental restorative composition.

Examples of the thiol compounds include 3-mercaptopropyltrimethoxysilane, 2-mercaptobenzoxazole, decanethiol, and thiobenzoic acid.

The content of the polymerization accelerator is preferably, but not limited to, 0.01 to 10 parts by weight per 100 parts by weight of the polymerizable monomer (A). The content is more preferably 0.1 to 7 parts by weight and even more preferably 0.2 to 5 parts by weight.

The inorganic filler (C) that has a refractive index (Cd) of 1.48 to 1.60 can be preferably used, and examples thereof include various glasses and aggregated particles, if the refractive index (Cd) of the inorganic filler (C) is too low, there is likely to be a large difference between the refractive index (Ad) of a polymer of the polymerizable monomer (A) and the refractive index (Cd) of the inorganic filler (C), and thus a cured product of the dental restorative composition may fail to have good transparency Too high a refractive index (Cd) is also likely to result in a large difference from the refractive index (Ad) of a polymer of the polymerizable monomer (A) and thus may cause a cured product of the dental restorative composition to be a white, opaque product which lacks sufficient transparency. The refractive index (Cd) of the inorganic filler (C) is more preferably in the range of 1.50 to 1.59 and even more preferably in the range of 1.52 to 1.58, in terms of adjusting the difference from the refractive index of a polymer of the polymerizable monomer (A). In terms of allowing a cured product of the dental restorative composition to have good transparency, the absolute value of the difference between the refractive index (Ad) of a polymer of the polymerizable monomer (A) and the refractive index (Cd) of the inorganic filler (C) is 0.01 or less. The refractive index (Cd) of the inorganic filler (C) can be measured by the method described in "EXAMPLES".

Examples of the various glasses (which contain silica as a main component and optionally contain an oxide of a heavy metal, boron, zirconium, titanium, aluminum, or the like) include: powders of glasses having a typical composition, such as molten silica, quartz, soda-lime silica glass, E glass, C glass, and borosilicate glass (PYREX (registered trademark) glass); dental glass powders, including strontium-boroaluminosilicate glasses such as "E 3000" (manufactured by ESSTECH, Inc.), "GM27884" (manufactured by SCHOTT AG), and "8235 series (e.g., 8235 UF 0.7)" (manufactured by SCHOTT AG), barium silicate glasses such as "E 2000" (manufactured by ESSTECH, Inc.), lanthanum glass ceramics such as "GM31684" (manufactured by SCHOTT AG), and fluoroaluminosilicate glasses such as "GM35429", "G018-091", and "G018-117" (which are manufactured by SCHOTT AG); various ceramics; composite oxides; diatomite; kaolin; clay minerals (such as montmorillonite); activated white earth; synthetic zeolite; mica; calcium fluoride; ytterbium fluoride; yttrium fluoride; calcium phosphate; barium sulfate; zirconium dioxide; titanium dioxide; and hydroxyapatite. Among these, barium glass, silica-zirconia composite oxide, silica-titania composite oxide, silica-alumina-zirconia composite oxide, crystalline quartz, and ytterbium fluoride are preferable in terms of the refractive index.

One inorganic filler or a combination of two or more inorganic fillers can be used as the inorganic filler (C). The shape of the inorganic filler is not particularly limited. It is preferable to employ a spherical shape, an approximately-spherical shape, or an irregular shape. The term "approximately-spherical" as used herein means that particles of the filler are rounded in shape as observed in a unit area of field of view in a photograph of the filler taken by a scanning electron microscope (which will hereinafter be abbreviated as "SEM") and have an average aspect ratio of 0.6 or more when the average aspect ratio is calculated as an average of values obtained by dividing a diameter of each particle measured in a direction perpendicular to the maximum diameter of the particle by the maximum diameter. It is preferable to use an irregularly-shaped filler as the inorganic filler (C) in terms of increasing the mechanical strength of a cured product of the dental restorative composition. The inorganic filler (C) may consist of aggregated particles (aggregated filler) prepared by aggregating inorganic ultrafine particles or any of various glasses. Commonly-known inorganic ultrafine particles can be used as the inorganic ultrafine particles without any limitation. For example, inorganic fine particles usable in the organic-inorganic composite filler described later can be used.

In terms of achieving high polishability, abrasion resistance, and mechanical strength of a cured product of the dental restorative composition, the average particle diameter of the inorganic filler (C) is 0.1 to 1.0 µm, preferably 0.2 to 0.7 µm, and more preferably 0.15 to 0.7 µm. If the average particle diameter is too small, a paste of the dental restorative composition that has yet to be cured may have an increased stickiness and therefore degraded handling properties, and a cured product of the dental restorative composition may have a reduced mechanical strength. If the average particle diameter is too large, it may be difficult to impart a sufficient gloss to a cured product of the dental restorative composition even by final polishing. Even when a certain level of gloss is obtained, the gloss may not be maintained for a long time due to reduced gloss retention. The average particle diameter can be measured by the method described in "EXAMPLES".

The content of the inorganic filler (C) is preferably 20 to 500 parts by weight, more preferably 50 to 400 parts by weight, and even more preferably 100 to 300 parts by weight per 100 parts by weight of the polymerizable monomer (A). If the content is low, there may be a reduction in mechanical strength, while if the content is high, a paste of the dental restorative composition that has yet to be cured may have too high a hardness and therefore degraded handling properties.

In terms of strengthening the bond with the polymerizable monomer (A), the inorganic filler (C) may optionally be surface-treated with a commonly-known surface treatment agent such as a silane coupling agent before use. Examples of the surface treatment agent include organosilicon compounds such as γ-methacryloxyalkyltrimethoxysilane (the number of carbon atoms between the methacryloxy group and the silicon atom: 3 to 12), γ-methacryloxyalkyltriethoxysilane (the number of carbon atoms between the methacryloxy group and the silicon atom: 3 to 12), vinyltrimethoxysilane, vinylethoxysilane, and vinyitriacetoxysilane.

The amount of the surface treatment agent used for the treatment is preferably 0.05 to 100 parts by weight and more preferably 0.10 to 50 parts by weight per 100 parts by weight of the inorganic filler (C) to be surface-treated.

As for the technique for the surface treatment, commonly-known techniques can be used without particular limitation. Examples of the techniques include: a technique in which the surface treatment agent is applied by spraying to the inorganic filler under vigorous stirring; a technique in which the inorganic filler and the surface treatment agent are dispersed or dissolved in an appropriate solvent and then the solvent is removed; and a technique in which the alkoxy groups of the surface treatment agent are hydrolyzed into silanol groups in an aqueous solution with the help of an acid catalyst so that the surface treatment agent is attached to the surface of the inorganic filler in the aqueous solution, and water is then removed. In any of these techniques, heating, usually at 50 to 150° C., can be used to fully complete the reaction between the surface of the inorganic filler and the surface treatment agent and thereby accomplish the surface treatment.

The organic-inorganic composite filler of the present invention includes two types of organic-inorganic composite fillers having different average particle diameters, i.e., the organic-inorganic composite filler (D) and the organic-inorganic composite filler (E). The combined use of such organic-inorganic composite fillers having different average particle diameters results in good handling properties of a paste of the composition that has yet to be cured and allows a cured product of the composition to attain good light diffusion ability and transparency, in the present invention, an organic-inorganic composite filler refers to a filler including an inorganic filler and a polymer of a polymerizable monomer.

The average particle diameter of the organic-inorganic composite filler (D) is 1 µm or more and less than 10 µm and is preferably 2 µm to 8 µm. If the average particle diameter of the organic-inorganic composite filler (D) is too small, the dental restorative composition that has yet to be cured and is in the form of a paste may have an increased stickiness and therefore degraded handling properties. If the average particle diameter is too large, the dental restorative composition that has yet to be cured and is in the form of a paste may have an increased dryness and therefore degraded handling properties, and the dental restorative composition that has been cured may have a rough surface and therefore a degraded aesthetic quality.

The average particle diameter of the organic-inorganic composite filler (E) is in the range of 10 to 50 µm, preferably in the range of 12 to 40 µm, and more preferably in the range of 15 to 30 µm. If the average particle diameter is too small, the dental restorative composition will contain an increased amount of fine filler particles having a particle diameter of less than 10 µm. This may cause an increased stickiness, a reduced consistency, and therefore degraded handling properties of the dental restorative composition that has yet to be cured and is in the form a paste. If the average particle diameter is too large, the yet-to-be-cured dental restorative composition may take the form of a very dry paste and have degraded handling properties. Additionally, in this case, the dental restorative composition that has been cured may have a rough surface and therefore a degraded aesthetic quality.

In the present invention, the organic-inorganic composite fillers must have particular refractive indices. Specifically, the absolute value of the difference between the refractive index (Ad) of a polymer of the polymerizable monomer (A) and one of the refractive index (Dd) of the organic-inorganic composite filler (D) and the refractive index (Ed) of the organic-inorganic composite filler (E) is 0.01 or less, and the absolute value of the difference between the refractive index (Ad) and the other of the refractive indices (Dd) and (Ed) is 0.03 or more, preferably 0.04 or more. The absolute value of the latter difference in refractive index is preferably 0.1 or less and more preferably 0.08 or less. The feature that the refractive index (Dd) and the refractive index (Ed) have such a relationship with the refractive index (Ad) allows the dental restorative composition that has been cured to have transparency and at the same time have light diffusion ability and therefore good color compatibility with natural teeth. The refractive index (Dd) and the refractive index (Ed) can be measured by the method described in "EXAMPLES".

In an embodiment of the present invention, the absolute value of the difference between the refractive index (Dd) and the refractive index (Ad) is 0.01 or less, and the absolute value of the difference between the refractive index (Ed) and the refractive index (Ad) is 0.03 or more. If the absolute value of the difference between the refractive index (Dd) and the refractive index (Ad) is more than 0.01, a paste having a sufficient transparency may not be obtained. The absolute value of the difference between the refractive index (Ed) and the refractive index (Ad) is more preferably 0.04 or more, which is because the color compatibility of a cured product of the dental restorative composition with natural teeth may diminish if said absolute value is too small. The absolute value of the difference between the refractive index (Ed) and the refractive index (Ad) is preferably 0.1 or less and more preferably 0.08 or less, which is because the resulting cured product may have a reduced light transmittance, too high an opacity, and therefore a degraded aesthetic quality if said absolute value is too large. When the refractive index (Ad) is 1.50 to 1.59, the refractive index (Dd) is preferably in the range of 1.50 to 1.59 and more preferably in the range of 1.52 to 1.58. When the refractive index (Ad) is 1.50 to 1.59, the refractive index (Ed) is preferably in the range of 1.45 to 1.49 and more preferably in the range of 1.47 to 1.49.

In general, the refractive index (Dd) of the organic-inorganic composite filler (D) is preferably in the range of 1.45 to 1.60, more preferably in the range of 1.49 to 1.59, and even more preferably in the range of 1.49 to 1.55.

The refractive index (Ed) of the organic-inorganic composite filler (E) is preferably in the range of 1.45 to 1.60, more preferably in the range of 1.45 to 1.55, and even more preferably in the range of 1.48 to 1.55.

The total amount of the organic-inorganic composite fillers is preferably 125 to 750 parts by weight, more preferably 125 to 600 parts by weight, even more preferably 125 to 500 parts by weight, particularly preferably 150 to 450 parts by weight, and more particularly preferably 200 to 400 parts by weight, per 100 parts by weight of the polymerizable monomer (A). If the total amount of the organic-inorganic composite filler (D) and the organic-inorganic composite filler (E) is too small, the dental restorative composition that has been cured may have a decreased light diffusion ability and therefore a reduced color compatibility with natural teeth. If the total amount is too large, the dental restorative composition that has yet to be cured may take the form of a very dry paste and have degraded handling properties, and the dental restorative composition that has been cured may have a rough surface and a degraded aesthetic quality.

The ratio between the contents of the organic-inorganic composite fillers, as expressed by (D):(E) in terms of weight ratio, is preferably in the range of 1:0.4 to 1:3.5, more preferably in the range of 1:0.6 to 1:3, even more preferably in the range of 1:0.7 to 1:2, and particularly preferably in the range of 1:0.8 to 1:1.8. When containing the organic-inorganic composite fillers in such a content ratio, the resulting paste is likely to have improved handling properties.

The content of the organic-inorganic composite filler (D) is preferably 100 to 500 parts by mass, more preferably 100 to 400 parts by weight, even more preferably 150 to 350 parts by weight, and particularly preferably 200 to 300 parts by weight, per 100 parts by weight of the polymerizable monomer (A). If the content of the organic-inorganic composite filler (D) is low when the refractive index (Dd) of the organic-inorganic composite filler (D) differs from the refractive index (Ad) of a polymer of the polymerizable monomer (A), the dental restorative composition that has been cured may have a decreased light diffusion ability and therefore a reduced color compatibility with natural teeth. If the content of the organic-inorganic composite filler (D) is high, the composition may take the form of a sticky paste and have degraded handling properties.

The content of the organic-inorganic composite filler (E) is preferably 25 to 400 parts by weight, more preferably 50 to 350 parts by weight, and even more preferably 100 to 300 parts by weight, per 100 parts by weight of the polymerizable monomer (A). If the content of the organic-inorganic composite filler (E) is low when the refractive index (Ed) of the organic-inorganic composite filler (E) differs from the refractive index (Ad) of the polymerizable monomer (A), the dental restorative composition that has been cured may have a decreased light diffusion ability and therefore a reduced color compatibility with natural teeth. If the content of the organic-inorganic composite filler (E) is high, the dental restorative composition that has yet to be cured may take the form of a very dry paste and have degraded handling properties, and the dental restorative composition that has been cured may have a rough surface and therefore a degraded aesthetic quality.

The transparencies ($\Delta L^*$) of the organic-inorganic composite filler (D) and the organic-inorganic composite filler (E) are preferably 30 or more, more preferably 33 or more, and even more preferably 36 or more. If the transparencies of these organic-inorganic composite fillers are low, the dental restorative composition may have a reduced transparency and the dental restorative composition that has been cured may have a degraded aesthetic quality. The organic-inorganic composite fillers are powders, and hence their transparencies cannot be measured directly. The transparency ($\Delta L^*$) of each organic-inorganic composite filler is determined as a value of the transparency measured for a cured product of a composition prepared in a paste form by mixing 100 parts by weight of the organic-inorganic composite filler into 100 parts by weight of a monomer solution prepared by mixing 1 part by weight of 2,4,6-trimethylbenzoyldiphenylphosphine oxide as a polymerization initiator with 100 parts by weight of a polymerizable monomer or polymerizable monomer mixture that, when cured, exhibits a refractive index equal to the refractive index of the filler. A specific method that can be used is the method described in "EXAMPLES".

The method for fabricating each of these organic-inorganic composite fillers is not particularly limited. For example, the fabrication may be done by first mixing a polymerizable monomer (A)' and a polymerization initiator (B)' into a commonly-known inorganic filler (C)' to form a paste, then allowing the paste to undergo solution polymerization, suspension polymerization, emulsion polymerization, or bulk polymerization, and finally crushing the resulting polymer.

The polymerizable monomer (A)' used in the organic-inorganic composite filler is not particularly limited. Any of the polymerizable monomers mentioned as examples of the polymerizable monomer (A) may be used, or a polymerizable monomer having the same composition as the polymerizable monomer (A) may be used. It is preferable to use a polymerizable monomer subjected to a purification process. If a polymerizable monomer not subjected to any purification process is used, the impurities in the polymerizable monomer may color the organic-inorganic composite filler, resulting in not only a failure of adjustment to a desired color but also a degradation in aesthetic quality of the dental restorative composition that has been cured.

The polymerization initiator (B)' used in the organic-inorganic composite filler is not particularly limited, and a commonly-known polymerization initiator can be used. Examples include polymerization initiators for photopolymerization using ultraviolet light or visible light and polymerization initiators for chemical polymerization using a reaction of a peroxide with an accelerator or heating. The polymerization initiator (B)' can be optionally selected from among the polymerization initiators mentioned as examples of the polymerization initiator (B).

The average particle diameter of the inorganic filler (C)' included in the organic-inorganic composite filler is preferably, but not limited to, a value equal to or less than the average particle diameter of the inorganic filler (C). If the average particle diameter of the inorganic filler (C)' included in the organic-inorganic composite filler is more than the average particle diameter of the inorganic filler (C), the dental restorative composition that has been cured may fail to have good polishability. Specifically, the average particle diameter of the inorganic filler (C)' is preferably 0.005 to 1.0 µm and more preferably 0.005 to 0.4 µm.

The material of the inorganic filler (C)' is not particularly limited, and any of the inorganic fillers mentioned as examples of the inorganic filler (C) may be used, or inorganic ultrafine particles may be used. One of the organic-inorganic composite fillers (D) and (E) preferably includes an inorganic filler having a refractive index equal to the refractive index of the inorganic filler (C), and more preferably includes a filler made of the same material as the inorganic filler (C). The inorganic filler (C)' may optionally be surface-treated with a commonly-known surface treatment agent such as a silane coupling agent before use, in terms of improving the affinity to the polymerizable monomer or enhancing the chemical bonding to the polymerizable monomer and thereby increasing the mechanical strength of the organic-inorganic composite filler. As for the surface treatment agent and the surface treatment technique, any of the treatment agents and techniques mentioned as examples for the inorganic filler (C) can be used without any limitation.

Commonly-known inorganic ultrafine particles may be used as the inorganic ultrafine particles without any limitation. Preferred examples include: particles of inorganic oxides such as silica, alumina, titania, and zirconia; composite oxide particles of these inorganic oxides; and particles of calcium phosphate, hydroxyapatite, yttrium fluoride, and ytterbium fluoride. More preferred are particles of silica, alumina, or titania which are fabricated by flame pyrolysis. Examples of such particles include those manufactured by Nippon Aerosil Co., Ltd. under the trade names Aerosil, Aeroxide AluC, Aeroxide $TiO_2P25$, Aeroxide $TiO_2P25S$, VP Zirconium Oxide 3-YSZ, and VP Zirconiumxide 3-YSZ PH.

The average particle diameter of the inorganic ultrafine particles is preferably 5 to 50 nm and more preferably 10 to 40 nm. The average particle diameter of the inorganic ultrafine particles can be measured by taking an electron microscope photograph of the inorganic ultrafine particles and calculating the average of the particle diameters of 100 or more ultrafine particles randomly-selected from the photographed particles. When the inorganic ultrafine particles are non-spherical, the particle diameter of each inorganic ultrafine particle is defined as an arithmetic average of the maximum and minimum lengths of the particle.

Given that the inorganic ultrafine particles are used in combination with the polymerizable monomer (A)' in the organic-inorganic composite filler, it is preferable to surface-treat the inorganic ultrafine particles with a surface treatment agent beforehand in order to improve the affinity to the polymerizable monomer (A)' or enhance the chemical bonding to the polymerizable monomer (A') and thereby increase the mechanical strength of the organic-inorganic composite filler. As for the surface treatment agent and the surface treatment technique, the treatment agents and techniques mentioned as examples for the inorganic filler (C) can be used without any limitation.

A commonly-known polymerization inhibitor, pH adjuster, ultraviolet absorber, antioxidant, antibacterial agent, fluorescent agent, surface-active agent, dispersant, or thickener can be further added as a component of the organic-inorganic composite filler depending on the purpose, as long as such a component does not diminish the effect of the invention.

Examples of the polymerization inhibitor that can be added to the organic-inorganic composite filler include 2,6-di-butylhydroxytoluene, hydroquinone, dibutylhydroquinone, dibutylhydroquinone monomethyl ether, and 2,6-t-butylphenol. These may be added alone or in combination with one another.

The ultraviolet absorber that can be added to the organic-inorganic composite filler may be a commonly-known compound, and examples thereof include triazine-based ultraviolet absorbers, benzotriazole-based ultraviolet absorbers, benzophenone-based ultraviolet absorbers, benzoate-based ultraviolet absorbers, and hindered amine-based light stabilizers. These may be added alone or in combination with one another.

To the dental restorative composition of the present invention, a component such as a polymerization inhibitor, a pH adjuster, an ultraviolet absorber, an antioxidant, an antibacterial agent, a fluorescent agent, a surface-active agent, a dispersant, or inorganic ultrafine particles can be further added depending on the purpose, as long as such a component does not diminish the effect of the invention. As for the polymerization inhibitor and the ultraviolet absorber, the polymerization inhibitors and ultraviolet absorbers mentioned as examples of those that can be added to the organic-inorganic composite filler can be used without any limitation.

With the dental restorative composition of the present invention, it is possible to obtain a cured product having good light diffusion ability and high color compatibility with natural teeth.

The "light diffusion ability" refers to the ability of a semi-transparent material such as a dental restorative composition to refract or reflect light incident on the material by the filler in the material so that the light diffuses in various directions. The reflected and diffused light to be observed have a color reflecting the color tone or background color of the dental restorative composition. It is thus expected that the higher the light diffusion ability, the greater the effect of blurring the background color of the restorative material or blurring the boundary between the restorative material and a natural tooth and hence the higher the color compatibility with the natural tooth. A proposed index of the light diffusion ability is the diffusivity D defined by the formula below. A greater value of the diffusivity D indicates that the cured product has a higher light diffusion ability.

$$D=(I_{20}/\cos 20°+I_{70}/\cos 70°)/(2I_0)$$

(In the formula, I represents the intensity of light transmitted through a sample, and $I_0$, $I_{20}$, and $I_{70}$ respectively represent the intensities (amounts of light) in directions forming angles of 0°, 20°, and 70° with the direction perpendicular to the sample sheet (the direction of incident light)).

The measurement of these intensities (amounts of light) can be performed using a variable angle photometer or a goniophotometer.

The diffusivity D of a cured product of the dental restorative composition of the present invention is preferably in the range of 0.01 to 0.5. If the value of the diffusivity D is too small, this means that the dental restorative composition that has been cured has an insufficient light diffusion ability leading to the difficulty in achieving good color matching to natural teeth, while if the value of the diffusivity D is too large, this means that the light diffusion ability is so high as to cause a failure to achieve a sufficient transparency. That is, a cured product of the dental restorative composition of the present invention can have a light diffusion ability suitable for achieving good color matching to natural teeth. In terms of the color matching to natural teeth, the diffusivity D is more preferably in the range of 0.02 to 0.45 and even more preferably in the range of 0.03 to 0.4.

In another embodiment of the present invention, the absolute value of the difference between the refractive index (Ed) of the organic-inorganic composite filler (E) and the refractive index (Ad) of a polymer of the polymerizable monomer (A) is 0.01 or less, and the absolute value of the difference between the refractive index (Dd) of the organic-inorganic composite filler (D) and the refractive index (Ad) is 0.03 or more. If the absolute value of the difference between the refractive index (Ed) and the refractive index (Ad) is more than 0.01, a paste having a sufficient transparency may not be obtained. The absolute value of the difference between the refractive index (Dd) and the refractive index (Ad) is more preferably 0.04 or more, which is because the dental restorative composition that has been cured may fail to have a sufficient light diffusion ability if said absolute value is too small. The difference between the refractive index (Dd) and the refractive index (Ad) is preferably 0.1 or less and more preferably 0.08 or less, which is because the resulting cured product may have a reduced transparency and therefore a degraded aesthetic quality if said difference is too large. The refractive index (Dd) is preferably in the range of 1.45 to 1.49 and more preferably in the range of 1.47 to 1.49. The refractive index (Ed) is preferably 1.50 to 1.59 and more preferably 1.52 to 1.58.

The dental restorative composition of the present invention can be used in resinous prosthetic materials such as resins for tooth crowns, artificial teeth, resin inlays, and blocks for CAD/CAM and in resinous restorative materials such as composite resins and sealants.

EXAMPLES

Hereinafter, the present invention will be specifically described with reference to examples, to which the present invention is not limited. The polymerizable monomer (A), polymerizable monomer (A)', polymerization initiator (B), polymerization initiator (B)', polymerization accelerator, inorganic filler (C), and inorganic filler (C)' which were used in Production Examples, Examples, and Comparative Examples are as listed below.

Polymerizable Monomer (A) and Polymerizable Monomer (A)'

Bis-GMA: 2,2-bis[4-(3-methacryloyloxy-2-hydroxypropoxy)phenyl]propane

D2,6E: 2,2-bis[4-methacryloyloxypolyethoxyphenyl]propane

UDMA: 2,2,4-trimethylhexamethylenebis(2-carbamoyloxyethyl) dimethacrylate

3G: Triethylene glycol dimethacrylate

DD: 1,10-decanediol dimethacrylate

M-1: UDMA/DD (weight ratio: 70/30), refractive index of polymer of M-1: 1.510

M-2: UDMA13G (weight ratio: 70/30), refractive index of polymer of M-2: 1.514

M-3: BisGMA/UDMA/3G (weight ratio: 10/60/30), refractive index of polymer of M-3: 1.520

M-4: D2.6E/UDMA/DD (weight ratio: 40/30/30), refractive index of polymer of M-4: 1.532

M-5: BisGMA/D2.6E/3G (weight ratio: 15/50/35), refractive index of polymer of M-5: 1.52

M-6: BisGMA/D2.6E/UDMA (weight ratio: 15/50/35), refractive index of polymer of M-6: 1.548

Polymerization Initiator (B) and Polymerization Initiator (B)'

AIBN: Azobisisobutyronitrile

CQ: dl-camphorquinone

TMDPO: 2,4,6-trimethylbenzoyldiphenylphosphine oxide

Polymerization Accelerator

PDE: Ethyl N,N-dimethylaminobenzoate

Inorganic Filler (C)

[F-4]

In a three-neck flask were placed 100 g of GM27884 NF 180 grade (barium glass manufactured by SCHOTT AG, refractive index: 1.53, average particle diameter: 0.18 μm), 13 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-4.

[F-5]

In a three-neck flask were placed 100 g of GM27884 UF 0.4 grade (barium glass manufactured by SCHOTT AG, refractive index: 1.53, average particle diameter: 0.4 μm), 9.4 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-5.

[F-6]

In a three-neck flask were placed 100 g of GM27884 UF 2.0 grade (barium glass manufactured by SCHOTT AG, refractive index: 1.53, average particle diameter: 2.0 μm), 1 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-6'. F-6' and F-4 were uniformly mixed at a weight ratio of 1:4, and thus F-6 having an average particle diameter of 0.9 μm was obtained.

[F-7]

In a three-neck flask were placed 100 g of 8235 UF 0.7 grade (barium glass manufactured by SCHOTT AG, refractive index: 1.55, average particle diameter: 0.7 μm), 6 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-7.

[F-8]

In a three-neck flask were placed 100 g of a spherical silica-titania composite oxide (refractive index: 1.510, average particle diameter: 0.3 μm), 10 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-8.

[F-9]

In a three-neck flask were placed 100 g of a spherical silica-zirconia composite oxide (refractive index: 1.520, average particle diameter: 0.2 μm), 10 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-9.

[F-10]

In a three-neck flask were placed 100 g of GM27884 UF 0.7 grade (barium glass manufactured by SCHOTT AG, refractive index: 1.53, average particle diameter: 0.7 μm), 6 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-10.

[F-11]

In a three-neck flask were placed 100 g of GM27884 UF 1.0 grade (barium glass manufactured by SCHOTT AG, refractive index: 1.53, average particle diameter: 1.0 μm), 4 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-11

Inorganic Filler (C)'

[F-1]

In a three-neck flask were placed 100 g of OX-50 (Aerosil (registered trademark) OX-50 manufactured by Nippon Aerosil Co., Ltd., refractive index: 1.46, average particle diameter: 0.04 μm), 7 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-1.

[F-2]

In a three-neck flask were placed 100 g of Ar 50 (Aerosil (registered trademark) 50 manufactured by Nippon Aerosil Co., Ltd., refractive index: 1.46, average particle diameter: 0.03 μm), 10 g of γ-methacryloxypropyitrimethoxysilane, and 200 mL of a 0.3 weight % aqueous acetic acid. solution, which were stirred. at room temperature for 2 hours. Water was removed by freeze drying, followed by a heating treatment at 80° C. for 5 hours to obtain F-2.

[F-3]

In a three-neck flask were placed 100 g of Ar 130 (Aerosil (registered trademark) 130 manufactured by Nippon Aerosil Co., Ltd., refractive index: 1.46, average particle diameter: 0.02 μm), 20 g of γ-methacryloxypropyltrimethoxysilane, and 200 mL of a 0.3 weight % aqueous acetic acid solution, which were stirred at room temperature for 2 hours. Water was removed by freeze drying, followed by a heating treatment at 80° C. for 5 hours to obtain F-3.

The physical property evaluations in Production Examples, Examples, and Comparative Examples were made by the methods described hereinafter.

[Refractive Index of filler]

The refractive index of each of the fillers (the inorganic fillers and organic-inorganic composite fillers) was measured according to JIS K 0062 with some modifications. Specifically, the measurement was performed by an immersion method at a constant humidity and a room temperature of 23° C. using an Abbe refractometer and a sodium D line light source. Each of the liquids used was prepared to have a refractive index equal to the refractive index of the filler as a sample, and the refractive index of the liquid was regarded as the refractive index of the sample. The preparation of each liquid was performed in a 23° C. atmosphere in such a manner as to achieve the solvent composition for allowing the liquid containing the suspended sample to show the highest transparency as observed with naked eyes. The liquids used included diiodomethane containing dissolved sulfur, 1-bromonaphthalene, methyl salicylate, dimethylformamide, and 1-pentanol.

[Refractive Index of Polymer of Polymerizable Monomer]

The refractive indices of polymers of the polymerizable monomers (A) used in Examples and Comparative Examples were measured according to JIS K 0062. Specifically, the measurement was performed in a 23° C. atmosphere using an Abbe refractometer and a sodium D line light source. For the measurement, a slight amount of liquid was dropped on a surface (measurement surface) of a test specimen, and the test specimen was placed in close contact with the prism surface, with an edge of the test specimen facing toward the light source. The test specimen used for the measurement was prepared as follows: In 100 parts by weight of the polymerizable monomer (A) were dissolved 0.5 parts by weight of α-camphorquinone as a polymerization initiator and 1.0 part by weight of ethyl N,N-dimethylaminobenzoate as a polymerization accelerator, and the resulting solution was degassed and then allowed to undergo photopolymerization to yield a polymer, which was formed into a rectangular parallelepiped having dimensions of 5 mm×10 mm×20 mm. The liquids used included diiodomethane containing dissolved sulfur, 1-bromonaphthalene, methyl salicylate, dimethylformamide, and 1-pentanol.

[Transparency of Organic-Inorganic Composite Filler]

A monomer solution was prepared by mixing 1 part by weight of 2,4,6-trimethylbenzoyldiphenylphosphine oxide as a polymerization initiator into 100 parts by weight of a polymerizable monomer or polymerizable monomer mixture that, when cured, exhibits a refractive index equal to the refractive index of the organic-inorganic composite filler. The organic-inorganic composite filler in an amount of 100 parts by weight was added to 100 parts by weight of the monomer solution, and they were mixed together to obtain a composition in a paste form. A disc-shaped test specimen (20 mm diameter×1.0 mm) of a cured product of the composition was prepared. The chromaticity measurement was performed on the test specimen by means of a spectrophotometric colorimeter (CM-3610d, manufactured by KONICA MINOLTA, INC.) using Illuminant C and an observer angle of 2 degrees to determine a lightness (L*w) for the case where a standard white plate was set behind the test specimen and a lightness (L*b) for the case where a standard black plate was set behind the same test specimen. The difference between the two values of lightness (ΔL*=L*w−L*b) was calculated and used as a measure of the degree of transparency. A greater value of ΔL* indicates that the cured product has a higher degree of transparency. ΔL* is preferably 30 or more, more preferably 33 or more, and even more preferably 36 or more.

[Transparency of Cured Product of Dental Restorative Composition]

A disc-shaped test specimen (20 mm diameter×1.0 mm) of a cured product of each dental restorative composition was prepared. The chromaticity measurement was performed on the test specimen by means of a spectrophotometric colorimeter (CM-3610d, manufactured by KONICA MINOLTA, INC.) using Illuminant C and an observer angle of 2 degrees to determine a lightness (L*w) for the case where a standard white plate was set behind the test specimen and a lightness (L*b) for the case where a standard black plate was set behind the same test specimen. The difference between the two values of lightness (ΔL*=L*w−L*b) was calculated and used as a measure of the degree of transparency. A greater value of ΔL* indicates that the cured product has a higher degree of transparency. ΔL* is preferably 21 or more and more preferably 24 or more.

[Diffusivity of Cured Product of Dental Restorative Composition]

Each of the dental restorative compositions produced was charged into a mold (30 mm diameter×0.5 mm thickness) made of Teflon (registered trademark). Glass slides were pressed against the upper and lower surfaces of the composition, both of which were irradiated with light for 1 minute to cure the composition. The cured product was removed from the mold and then tested for transmitted light intensity distribution using a three-dimensional variable angle photometer (GP-200, manufactured by MURAKAMI COLOR RESEARCH LABORATORY). The diffusivity D was calculated according to the following formula.

$$D=\{(I_{20}/\cos 20°)+(I_{70}/\cos 70°)\}/(2\times I_0)$$

In the formula, I represents the intensity of light transmitted through a sample, and $I_0$, $I_{20}$, and $I_{70}$ respectively represent the amounts of light in directions forming angles of 0°, 20°, and 70° with the direction of incident light. The trigonometric functions each represent a cosine in the direction for which the intensity was measured, and the unit of angle is degree.

The diffusivity D as determined by the above formula is preferably 0.03 or more and more preferably 0.2 or more.

[Polishability]

Each curable paste was charged into a prismatic mold of 2 mm width×4 mm height×20 mm length and cured by thorough photopolymerization, after which the cured product was removed from the mold and immersed in 37° C. water for 24 hours. The surface of this sample piece was polished with #1500 waterproof abrasive paper and then subjected to final polishing with Sof-Lex Superfine (manufactured by 3M) for 1 minute. The gloss of the surface was measured using a glossmeter (VG-2000, manufactured by NIPPON DENSHOKU INDUSTRIES CO., LTD.), the ratio of the gloss (gloss value) relative to the gloss of a mirror defined as 100% was determined, and the ratio was used as a measure of the polish ability. The measurement angle was 60 degrees. For the polishability, the gloss value is preferably 65% or more and more preferably 70% or more.

[Handling Properties of Paste]

The properties of pastes of the dental restorative compositions that had yet to be cured were evaluated in terms of ease of handling on the basis of the following criteria. That is, a less sticky paste was rated as "Good", a particularly less sticky paste was rated as "Excellent", and a very sticky paste difficult to handle was rated as "Poor". Additionally, a less dry paste was rated as "Good", a particularly less dry paste was rated as "Excellent", and a very dry paste difficult to handle was rated as "Poor".

[Average Particle Diameter of Filler]

The average particle diameters of the inorganic fillers and organic-inorganic composite fillers were measured with a laser diffraction particle size distribution analyzer (SALD-2100, manufactured by Shimadzu Corporation). The dispersion medium used was a 0.2% aqueous solution of sodium hexa etaphosphate.

The organic-inorganic composite fillers were fabricated in the manner as described in Production Examples 1 to 7 below.

Production Example 1

An inorganic filler (C)' (F-1) in an amount of 100 parts by weight was added to 100 parts by weight of a polymerizable monomer (A)' (M-1) in which 1 weight % of AIBN was dissolved beforehand as a polymerization initiator (B)' (filler content=50 weight %), and they were mixed together into a paste. This paste was allowed to undergo heat polymerization at a reduced pressure at 100° C. for 5 hours. The resulting cured polymer was crushed with a vibrating ball mill until the desired average particle diameter was obtained. The resulting crushed filler in an amount of 100 g was surface-treated in 200 ml of an ethanol solution containing 2 weight % of γ-methacryloyloxypropyltrimethoxysilane under reflux at 90° C. for 5 hours, thus obtaining an organic-inorganic composite filler. The refractive index and transparency of the organic-inorganic composite filler obtained were measured. The results are shown in Table 1.

Production Example 2 to Production Example 7

In Production Examples 2 to 7, organic-inorganic composite fillers were fabricated in the same manner as in Production Example 1 according to the details in Table 1. The refractive indices and transparencies of the organic-inorganic composite fillers obtained were measured. The results are shown in Table 1.

TABLE 1

| | Inorganic filler (C)' | | | Organic-inorganic composite filler | | | |
|---|---|---|---|---|---|---|---|
| | Code | Refractive index | Average particle diameter (μm) | Polymerizable monomer (A)' Code | Filler content (weight %) | Refractive index | Transparency (ΔL*) |
| Production Example 1 | F-1 | 1.46 | 0.04 | M-1 | 50 | 1.48 | 32 |
| Production Example 2 | F-2 | 1.46 | 0.03 | M-2 | 30 | 1.49 | 31 |
| Production Example 3 | F-3 | 1.46 | 0.02 | M-1 | 60 | 1.48 | 34 |
| Production Example 4 | F-4 | 1.53 | 0.18 | M-4 | 65 | 1.53 | 39 |
| Production Example 5 | F-6 | 1.53 | 0.9 | M-4 | 50 | 1.53 | 39 |
| Production Example 6 | F-7 | 1.55 | 0.7 | M-5 | 65 | 1.55 | 38 |
| Production Example 7 | F-8 | 1.51 | 0.3 | M-1 | 60 | 1.51 | 34 |

Example 1

A polymerization initiator (B) (TMDPO) in an amount of 0.3 parts by weight was thoroughly dissolved in 15 parts by weight of a polymerizable monomer (A) (M-4). Subsequently, the solution, 25 parts by weight of an inorganic filler (C) (F-4, refractive index: 1.53, average particle diameter: 0.18 μm, treated with 7% γ-methacryloxypropyltrimethoxysilane), 30 parts by weight of an organic-inorganic composite filler (D) obtained by the method of Production Example 4 (refractive index: 1.53, average particle diameter: 4 μm), and 30 parts by weight of an organic-inorganic composite filler (E) obtained by the method of Production Example 1 (refractive index: 1.48, average particle diameter: 15 μm) were kneaded together using an agate mortar to form a homogeneous, curable paste. Tiny air bubbles were then removed from this paste at a reduced pressure, and the various physical properties of the paste were evaluated by the methods described above. The composition ratios (parts by weight) and the evaluation results are shown in Table 2.

Examples 2 to 15, Comparative Examples 1 to 4

Dental restorative compositions of Examples 2 to 15 and Comparative Examples 1 to 4 were prepared in the same manner as that of Example 1 using the composition ratios (parts by weight) shown in Table 2 and Table 3, and the various physical properties of the compositions were evaluated. The results are shown in Tables 2 and 3.

In Table 2 and Table 3, "Handling properties" refers to the handling properties of pastes of the dental restorative compositions that had yet to be cured, while "Polishability", "Transparency", and "Diffusivity" refer to those of cured products of the dental restorative compositions.

In Comparative Example 1, the dental restorative composition that had yet to be cured was very sticky and disadvantageous in terms of handling. In Comparative Example 2, in which the dental restorative composition did not contain the organic-inorganic composite filler (E), the cured product of the dental restorative composition showed a high transparency but lacked a light diffusion ability. In Comparative Example 3, in which the dental restorative composition did not contain the inorganic filler (C), the dental restorative composition that had yet to be cured was very dry and disadvantageous in terms of handling. In Comparative Example 4, the differences between the refractive index (Ad) of the polymer of the polymerizable monomer (A) and the refractive index (Cd) of the inorganic filler and between the refractive index (Ad) and the refractive index (Dd) of the organic-inorganic composite filler were more than 0.01, the reason for which the cured product lacked a sufficient transparency.

TABLE 2

| | | | Refractive index | | Example 1 | Example 2 | Example 3 | Example 4 | Example 5 |
|---|---|---|---|---|---|---|---|---|---|
| Polymerizable monomer (A) | | M-4 | Ad | 1.53 | 100 | 100 | — | — | 100 |
| | | M-3 | | 1.52 | — | — | 100 | 100 | — |
| | | M-1 | | 1.51 | — | — | — | — | — |
| Polymerization initiator (B) | | TMDPO | | | 2 | 1 | — | 10 | 1 |
| | | CQ | | | — | — | 0.2 | 0.3 | — | 0.2 |
| Polymerization accelerator | | PDE | | | — | — | 0.2 | 0.4 | — | 0.2 |
| Inorganic filler (C) | F-4 | Average particle diameter: 0.18 μm | Cd | 1.53 | 166 | — | — | — | — |
| | F-5 | Average particle diameter: 0.4 μm | | | — | 300 | — | — | — |
| | F-10 | Average particle diameter: 0.7 μm | | | — | — | — | 150 | — |
| | F-11 | Average particle diameter: 1 μm | | | — | — | 233 | — | — |
| | F-6 | Average particle diameter: 0.9 μm | | | — | — | — | — | 220 |
| Organic-inorganic composite filler (D) | Production Example 4 | Average particle diameter: 4 μm | Dd | 1.53 | 200 | — | — | — | — |
| | | Average particle diameter: 8 μm | | | — | 200 | — | — | 150 |
| | | Average particle diameter: 9 μm | | | — | — | 200 | 450 | — |
| Organic-inorganic composite filler (E) | Production Example 1 | Average particle diameter: 15 μm | Ed | 1.48 | 200 | — | — | — | — |
| | | Average particle diameter: 20 μm | | | — | 400 | — | — | 60 |
| | | Average particle diameter: 35 μm | | | — | — | 133 | — | — |
| | | Average particle diameter: 40 μm | | | — | — | — | 300 | — |
| Difference in refractive index | | [Cd − Ad] | | | 0 | 0 | 0.01 | 0.01 | 0 |
| | | [Dd − Ad] | | | 0 | 0 | 0.01 | 0.01 | 0 |
| | | [Ed − Ad] | | | 0.05 | 0.05 | 0.04 | 0.04 | 0.05 |
| Handling properties | | Dryness | | | Excellent | Excellent | Excellent | Excellent | Excellent |
| | | Stickiness | | | Excellent | Excellent | Excellent | Excellent | Excellent |
| | | Polishability | | | 84 | 78 | 65 | 68 | 72 |
| | | Transparency | | | 27 | 25 | 27 | 26 | 27 |
| | | Diffusivity | | | 0.25 | 0.27 | 0.22 | 0.26 | 0.23 |
| | | Weight ratio (D):(E) | | | 1:1 | 1:2 | 1:0.67 | 1:0.67 | 1:0.4 |

TABLE 2-continued

|  |  |  | Refractive index | Comparative Example 1 | Comparative Example 2 | Comparative Example 3 | Comparative Example 4 |
|---|---|---|---|---|---|---|---|
| Polymerizable monomer (A) | M-4 | Ad | 1.53 | 100 | 100 | 100 | — |
|  | M-3 |  | 1.52 | — | — | — | — |
|  | M-1 |  | 1.51 | — | — | — | 100 |
| Polymerization initiator (B) | TMDPO |  | — | 0.5 | 1 | 1 | — |
|  | CQ |  | — | 0.1 | 0.2 | 0.2 | 0.3 |
| Polymerization accelerator | PDE |  | — | 0.1 | 0.2 | 0.2 | 0.4 |
| Inorganic filler (C) | F-4 | Average particle diameter: 0.18 μm | Cd 1.53 | — | — | — | — |
|  | F-5 | Average particle diameter: 0.4 μm |  | 240 | 300 | — | — |
|  | F-10 | Average particle diameter: 0.7 μm |  | — | — | — | — |
|  | F-11 | Average particle diameter: 1 μm |  | — | — | — | 233 |
|  | F-6 | Average particle diameter: 0.9 μm |  | — | — | — | — |
| Organic-inorganic composite filler (D) | Production Example 4 | Average particle diameter: 4 μm | Dd 1.53 | — | — | 333 | — |
|  |  | Average particle diameter: 8 μm |  | — | 600 | — | — |
|  |  | Average particle diameter: 9 μm |  | — | — | — | 200 |
| Organic-inorganic composite filler (E) | Production Example 1 | Average particle diameter: 15 μm | Ed 1.48 | 160 | — | — | — |
|  |  | Average particle diameter: 20 μm |  | — | — | 233 | — |
|  |  | Average particle diameter: 35 μm |  | — | — | — | 133 |
|  |  | Average particle diameter: 40 μm |  | — | — | — | — |
| Difference in refractive index | [Cd − Ad] |  |  | 0 | 0 | — | 0.02 |
|  | [Dd − Ad] |  |  | — | 0 | 0 | 0.02 |
|  | [Ed − Ad] |  |  | 0.05 | — | 0.05 | 0.03 |
| Handling properties | Dryness |  |  | Good | Good | Poor | Excellent |
|  | Stickiness |  |  | Poor | Good | Excellent | Excellent |
| Polishability |  |  |  | 75 | 70 | 78 | 65 |
| Transparency |  |  |  | 25 | 39 | 22 | 17 |
| Diffusivity |  |  |  | 0.23 | 0 | 0.25 | 0.22 |
| Weight ratio (D):(E) |  |  |  | — | — | 1:0.70 | 1:0.67 |

TABLE 3

|  |  |  | Refractive index | Example 6 | Example 7 | Example 8 | Example 9 | Example 10 |
|---|---|---|---|---|---|---|---|---|
| Polymerizable monomer (A) | M-1 |  | Ad 1.51 | — | — | — | — | — |
|  | M-2 |  | 1.51 | — | — | — | — | — |
|  | M-3 |  | 1.52 | — | — | — | — | — |
|  | M-4 |  | 1.53 | — | — | — | 100 | 100 |
|  | M-5 |  | 1.55 | 100 | 100 | — | — | — |
|  | M-6 |  | 1.55 | — | — | 100 | — | — |
| Polymerization initiator (B) | TMDPO |  | — | 0.2 | 0.2 | 0.15 | 0.15 | 0.15 |
| Inorganic filler (C) | F-4 | Average particle diameter: 0.18 μm | Cd 1.53 | — | — | — | 75 | 200 |
|  | F-6 | Average particle diameter: 0.9 μm | 1.53 | — | — | — | — | — |
|  | F-7 | Average particle diameter: 0.7 μm | 1.55 | 133 | 200 | 40 | — | — |
|  | F-8 | Average particle diameter: 0.3 μm | 1.51 | — | — | — | — | — |
|  | F-9 | Average particle diameter: 0.2 μm | 1.52 | — | — | — | — | — |
| Organic-inorganic composite filler (D) | Production Example 2 | Average particle diameter: 9 μm | Dd 1.49 | — | — | — | 125 | — |
|  | Production Example 5 | Average particle diameter: 6 μm | 1.53 | — | — | — | — | 50 |
|  | Production Example 6 | Average particle diameter: 3 μm | 1.55 | 233 | — | 185 | — | — |
|  | Production Example 7 | Average particle diameter: 4 μm | 1.51 | — | 133 | — | — | — |

TABLE 3-continued

|  |  |  |  |  |  |  |  |  |
|---|---|---|---|---|---|---|---|---|
| Organic-inorganic composite filler (E) | Production Example 1 | Average particle diameter: 19 µm | Ed | 1.48 | — | — | 175 | — | — |
|  | Production Example 3 | Average particle diameter: 18 µm |  | 1.48 | — | — | — | — | 150 |
|  | Production Example 4 | Average particle diameter: 25 µm |  | 1.53 | — | — | — | 200 | — |
|  | Production Example 6 | Average particle diameter: 11 µm |  | 1.55 | — | 233 | — | — | — |
|  | Production Example 7 | Average particle diameter: 21 µm |  | 1.51 | 200 | — | — | — | — |
| Difference in refractive index |  | [Cd − Ad] |  |  | 0 | 0 | 0 | 0 | 0 |
|  |  | [Dd − Ad] |  |  | 0 | 0.04 | 0 | 0.04 | 0 |
|  |  | [Ed − Ad] |  |  | 0.04 | 0 | 0.07 | 0 | 0.05 |
| Handling properties |  | Dryness |  |  | Excellent | Excellent | Excellent | Good | Excellent |
|  |  | Stickiness |  |  | Excellent | Excellent | Good | Excellent | Good |
|  |  | Polishability |  |  | 68 | 66 | 70 | 94 | 74 |
|  |  | Transparency |  |  | 34 | 35 | 25 | 34 | 26 |
|  |  | Diffusivity |  |  | 0.25 | 0.22 | 0.32 | 0.25 | 0.27 |
|  |  | Weight ratio (D):(E) |  |  | 1:0.86 | 1:1.75 | 1:0.95 | 1:1.6 | 1:3 |

|  |  |  | Refractive index | Example 11 | Example 12 | Example 13 | Example 14 | Example 15 |
|---|---|---|---|---|---|---|---|---|
| Polymerizable monomer (A) | M-1 |  | Ad 1.51 | — | — | — | — | 100 |
|  | M-2 |  | 1.51 | — | — | — | 100 | — |
|  | M-3 |  | 1.52 | — | 100 | 100 | — | — |
|  | M-4 |  | 1.53 | 100 | — | — | — | — |
|  | M-5 |  | 1.55 | — | — | — | — | — |
|  | M-6 |  | 1.55 | — | — | — | — | — |
| Polymerization initiator (B) | TMDPO |  | — | 0.2 | 0.2 | 0.2 | 0.17 | 0.3 |
| Inorganic filler (C) | F-4 | Average particle diameter: 0.18 µm | Cd 1.53 | 166 | — | — | — | — |
|  | F-6 | Average particle diameter: 0.9 µm | 1.53 | — | — | — | — | — |
|  | F-7 | Average particle diameter: 0.7 µm | 1.55 | — | — | — | — | — |
|  | F-8 | Average particle diameter: 0.3 µm | 1.51 | — | — | — | — | 500 |
|  | F-9 | Average particle diameter: 0.2 µm | 1.52 | — | 66 | 100 | 150 | — |
| Organic-inorganic composite filler (D) | Production Example 2 | Average particle diameter: 9 µm | Dd 1.49 | — | — | 267 | — | — |
|  | Production Example 5 | Average particle diameter: 6 µm | 1.53 | 133 | — | — | — | — |
|  | Production Example 6 | Average particle diameter: 3 µm | 1.55 | — | — | — | — | — |
|  | Production Example 7 | Average particle diameter: 4 µm | 1.51 | — | 300 | — | 167 | 150 |
| Organic-inorganic composite filler (E) | Production Example 1 | Average particle diameter: 19 µm | Ed 1.48 | — | 200 | — | 139 | — |
|  | Production Example 3 | Average particle diameter: 18 µm | 1.48 | 267 | — | — | — | 250 |
|  | Production Example 4 | Average particle diameter: 25 µm | 1.53 | — | — | — | — | — |
|  | Production Example 6 | Average particle diameter: 11 µm | 1.55 | — | — | — | — | — |
|  | Production Example 7 | Average particle diameter: 21 µm | 1.51 | — | — | 200 | — | — |
| Difference in refractive index |  | [Cd − Ad] |  | 0 | 0 | 0 | 0.01 | 0 |
|  |  | [Dd − Ad] |  | 0 | 0.01 | 0.03 | 0 | 0 |
|  |  | [Ed − Ad] |  | 0.05 | 0.04 | 0.01 | 0.03 | 0.03 |
| Handling properties |  | Dryness |  | Excellent | Excellent | Excellent | Excellent | Excellent |
|  |  | Stickiness |  | Excellent | Excellent | Excellent | Excellent | Excellent |
|  |  | Polishability |  | 69 | 84 | 86 | 83 | 84 |
|  |  | Transparency |  | 25 | 31 | 26 | 25 | 28 |
|  |  | Diffusivity |  | 0.29 | 0.23 | 0.22 | 0.22 | 0.23 |
|  |  | Weight ratio (D):(E) |  | 1:2 | 1:0.67 | 1:0.75 | 1:0.83 | 1:1.67 |

The invention claimed is:

1. A dental restorative composition comprising:
   a polymerizable monomer (A):
   a polymerization initiator (B);
   an inorganic filler (C) having an average particle diameter of 0.1 to 1 μm: and
   an organic-inorganic composite filler, wherein
   the organic-inorganic composite filler comprises
      an organic-inorganic composite filler (D) having an average particle diameter of 1 μm or more and less than 10 μm, and
      an organic-inorganic composite filler (D) having an average particle diameter of 10 to 50 μm,
   an absolute value of a difference between a refractive index (Cd) of the inorganic filler (C) and a refractive index (Ad) of a polymer of the polymerizable monomer (A) is 0.01 or less,
   an absolute value of a difference between the refractive index (Ad) and one of a refractive index (Dd) of the organic-inorganic composite filler (D) and a refractive index (Ed) of the organic-inorganic composite filler (E) is 0.01 or less, and
   an absolute value of a difference between the refractive index (Ad) and the other of the refractive index (Dd) and the refractive index (Ed) is 0.03 or more.

2. The dental restorative composition according to claim 1, wherein the average particle diameter of the inorganic filler (C) is 0.2 to 0.7 μm.

3. The dental restorative composition according to claim 1, wherein one of the organic-inorganic composite filler (D) and the organic-inorganic composite filler (E) comprises an inorganic filler having a refractive index equal to the refractive index of the inorganic filler (C).

4. The dental restorative composition according to claim 1, wherein the organic-inorganic composite filler (D) and the organic-inorganic composite filler (E) each have a transparency ($\Delta L^*$) of 30 or more.

* * * * *